United States Patent [19]

Breinholt et al.

[11] Patent Number: 5,596,015

[45] Date of Patent: Jan. 21, 1997

[54] FUNGICIDALLY ACTIVE COMPOUNDS

[75] Inventors: Jens Breinholt, Bagsvaerd; Lene Lange, Valby, both of Denmark

[73] Assignee: Novo Nordisk A/S, Bagsvaerd, Denmark

[21] Appl. No.: 347,336

[22] Filed: Dec. 2, 1994

[30] Foreign Application Priority Data

Jun. 24, 1993 [DK] Denmark .................. 836/93

[51] Int. Cl.$^6$ .................. C12P 17/04; C07D 307/46
[52] U.S. Cl. .................. 514/473; 426/545; 435/126; 435/254.1; 435/911; 549/295; 549/297; 549/313
[58] Field of Search .................. 435/126, 911, 435/254.1; 549/295, 297, 313; 514/473; 426/545

[56] References Cited

FOREIGN PATENT DOCUMENTS 2101637  1/1971  Germany .

OTHER PUBLICATIONS

G. Pattenden, Fortschritte de Chemie Organischer Naturstoffe, pp. 133–198, 1978.
Ballio et al., Physiological Plant Pathology, vol. 8, pp. 163–169, 1976.
Ballio et al., Biochimica et Biophysica Acta, vol. 573, pp. 51–60, 1979.
Gedge et al., J.C.S. Chem. Comm., pp. 880–882, 1978.
Rehse et al., Archiv der Pharmazie, 316, pp. 115–120, 1983.
Ballio et al., Specialia, pp. 349–350, 1970.

*Primary Examiner*—Herbert J. Lilling
*Attorney, Agent, or Firm*—Steve T. Zelson, Esq.; Cheryl H. Agris, Esq.

[57] ABSTRACT

Compounds having formula (3), wherein $R^1$ is hydrogen, straight or branched alkyl with 1–10 carbon atoms, straight or branched alkenyl with 2–10 carbon atoms, straight or branched alkynyl with 2–10 carbon atoms, benzyl or aryl, optionally mono- or plurisubstituted with straight or branched alkyl with 1-10 carbon atoms, hydroxy, alkoxy, halogen, an amino or a nitro group; and when $R^1$ is H salts thereof, or $R^1$ is acyl ($R^1$=—$COR^2$) wherein $R^2$ is straight or branched alkyl with 1–10 carbon atoms, alkenyl with 2–10 carbon atoms, alkynyl with 2–10 carbon atoms, or aryl, optionally mono- or plurisubstituted with alkyl with 1-10 carbon atoms, hydroxy, alkoxy, halogen, an amino or a nitro group. Compounds of formula (3) have interesting antifungal activities and may, accordingly, be used as active ingredients in fungicidal compositions.

23 Claims, No Drawings

FUNGICIDALLY ACTIVE COMPOUNDS

CROSS-REFERENCE TO RELATED APPLICATIONS

This application is a National Stage under 35USC371 of PCT/DK93/00190 filed Jun. 2, 1993.

FIELD OF THE INVENTION

The present invention relates to fungicidally active compounds and methods for their preparation as well as microorganisms capable of producing such compounds. Furthermore, the invention relates to fungicidal compositions comprising these compounds, either alone or in combination with other biocides or growth regulators, and to the use of the compounds or compositions of the invention for controlling fungi.

The compounds of the invention belong to a sub-group of the well-known tetronic acids having the general formula 1 as shown below, namely the 4-ylidene tetronic acids with the general formula 2.

BACKGROUND OF THE INVENTION

It is well known that various microorganisms are capable of producing metabolites associated with interesting biological activities. Such compounds are of potential interest for use in, e.g. the agricultural field where they are considered to constitute environmentally desirable alternatives to synthetically prepared compounds normally used, e.g. as biocides for controlling diseases and pests in valuable crops.

Although the search for such microbial metabolites has been a growing area of research during the last decade, only a minor number of useful biologically active metabolites has been identified and most biocides employed today are still synthetical compounds.

4-Ylidene tetronic acids with the general formula 2, is a rather newly discovered group of natural products. The distribution, synthesis, biosynthesis and biological activities of these compounds has been reviewed by Pattenden[1].

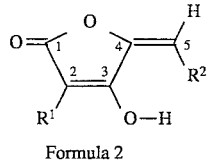

Formula 2

These compounds are a sub-group of the tetronic acids with the general formula 1, which include biologically important natural products, such as vitamin C (i.e. a compound of formula 1 wherein $R^1$=OH and $R^2$=CHOHCH$_2$OH).

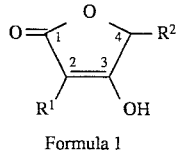

Formula 1

A variety of different biological activities have been reported for the tetronic acids, including antibiotic, anti-inflammatory, plant growth inhibitory, immunosuppressive and anti-coagulant effects[1,2,3]. However, the application of the compounds in therapy has often been precluded due to undesirable toxic side-effects.

The genus Fusiccocum is known as a producer of secondary metabolites; diterpenes[4] and fatty acid derivatives[5,6] have been reported from F. amygdali, but no compounds having structure and biological activity spectrum similar to the tetronic acids has been reported from said genus.

SUMMARY OF THE INVENTION

It was therefore surprising to find that the fungal species Fusiccocum is capable of producing novel compounds belonging to the 4-ylidene tetronic acids and having interesting fungicidal activities. The present invention is based on this finding.

Accordingly, in a first aspect the present invention relates to a compound having the formula 3

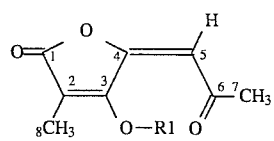

Formula 3 wherein $R^1$ is hydrogen, straight or branched alkyl with 1–10 carbon atoms, straight or branched alkenyl with 2–10 carbon atoms, straight or branched alkynyl with 2–10 carbon atoms, benzyl or aryl, optionally mono- or plurisubstituted with straight or branched alkyl with 1–10 carbon atoms, hydroxy, alkoxy, halogen, an amino or a nitro group; and when $R^1$ is H salts thereof, or $R^1$ is acyl ($R^1$=—$COR^2$) wherein $R^2$ is straight or branched alkyl with 1–10 carbon atoms, alkenyl with 2–10 carbon atoms, alkynyl with 2–10 carbon atoms, or aryl, optionally mono- or plurisubstituted with alkyl with 1–10 carbon atoms, hydroxy, alkoxy, halogen, an amino or a nitro group.

In a second aspect the present invention relates to a group of derivatives of the compounds of the invention having the formula 3, namely compounds having the general formula 4

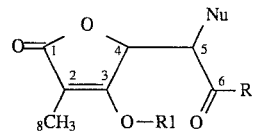

Formula 4 wherein $R^1$ is as defined above and Nu is halogen or —$OR^3$, —$SR^3$, —$NR^3R^{3'}$, wherein $R^3$ and $R^{3'}$, being identical or different, are as $R^1$ as defined above, and salts thereof.

Compounds of formula 4 are obtainable from compounds of formula 3 by addition of various nucleophilic species to C-5 as explained in further detail below.

In a specific aspect the present invention relates to a compound having the formula 5

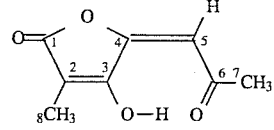

Formula 5 and salts thereof.

The compound of formula 5 is obtainable as a natural metabolite from a microorganism such as a fungus, especially a fungus of the genus Fusiccocum.

Furthermore, the present invention relates to processes for producing a compound of the invention, which either involves cultivation of microorganisms capable of producing the compounds or full or semi-synthetical preparation of the compounds.

In a further aspect the present invention relates to a fungicidal composition comprising, as an active ingredient, one or more of the novel compounds of the invention or, alternatively, a microorganism capable of producing such compounds. Further constituents of the composition are suitable excipients, such as diluents, carriers etc. and optionally, if desired, other biocidal and/or growth-promoting compounds.

In a further aspect the invention relates to a method of controlling fungi at a locus infested or liable to be infested therewith, which comprises applying to said locus an antifungal composition as defined above of the invention.

In a still further aspect, the invention relates to the use of the novel compounds for controlling plant diseases, especially fungal attack, and as preservatives and/or additives to control fungi in foods and feeds, timber and wood, paints, growth media, cosmetics etc.

Finally, the invention relates to an isolated pure culture of the microorganism Fusicoccum sp. L394-3 (IMI 351573) or a mutant thereof capable of producing a compound of the invention.

In the present context, the term "mutant" is intended to indicate any organism derived from the Fusiccocum sp. of the invention which has retained the capability of producing a compound of the invention. The mutant may be a natural mutant or one which is obtained by a synthetic process, e.g. by subjecting a culture of the microorganism of the invention to a conventional mutagenesis treatment.

DETAILED DESCRIPTION OF THE INVENTION

In connection with the compounds of the present invention, i.e. compounds with the general formula 3 or 4, the term "alkyl with 1–10 carbon atoms" is intended to include methyl, ethyl, propyl, butyl, pentyl, hexyl etc. straight, branched or cyclic where appropriate.

The term "alkenyl with 2–10 carbon atoms" is intended to include ethenyl, propenyl butenyl, pentenyl, hexenyl etc. straight, branched or cyclic where appropriate. Also polyenyl (dienyl, trienyl etc.) is inteded to be included in the term.

The term "alkynyl with 2–10 carbon atoms" is intended to include ethynyl, propynyl, butynyl pentynyl, hexynyl etc. straight, branched or cyclic where appropriate. Also polyynyl (diynyl, triynyl etc.) is inteded to be included in the term.

The term "aryl" is intended to include aromatic radicals like phenyl, naphtyl, phenantryl etc. and hetero aromatic radicals like furanyl, thiophenyl, pyridinyl, imidazolyl, oxazolyl etc.

Preferred mono- or plurisubstituted aryl moieties are 4-halo-, 4-hydroxy-, 4-methoxy- and 4-methyl-phenyl, 2,4-dihalo- and 2,4-dihydroxy- and 2,4-dimethoxy-phenyl.

The term "plurisubstituted" covers di-, tri-, tetra- or higher substitution.

The term "halogen" covers fluorine, chlorine, bromine and iodine.

Interesting compounds of the invention are compounds of formula 3, wherein $R^1$ is hydrogen, methyl, benzyl or acetyl. The compound of formula 3 in which $R^1$ is benzyl and the preparation thereof is described in Example 4 below.

A particularly preferred compound of the invention is the compound having the formula 5 shown above, i.e. the compound of formula 3 in which $R^1$ is hydrogen, and salts thereof. This compound and the preparation thereof is described in detail in Example 1 below.

As indicated above compounds with the general formula 4 constitute a novel group of derivatives of compounds having the general formula 3, i.e. derivatives in which various nucleophilic species have been added to C-5 of compounds with the general formula 3. A compound of formula 4 and the preparation thereof are described in Examples 3 below.

In a further aspect the present invention relates to a method of preparing a compound of the invention as defined above, comprising a) cultivating a microorganism capable of producing said compound in a suitable nutrient medium and under suitable conditions so as to obtain a biomass comprising the compound, and b) recovering the compound from the biomass and/or the culture medium.

The microorganism which is capable of producing compounds of the invention is normally a fungus, preferably of the class Deuteromycetes, and more preferably of the genus Fusicoccum. Strains of a Fusicoccum sp. found on a plant belonging to the genus Asphodelus, especially a plant of the species A. macrocarpus, are contemplated to be of particular interest, one specific example of such strain being the Fusicoccum sp. described herein having the deposition number IM CC No. 351573 or a mutant thereof capable of producing a compound of the invention.

A suitable nutrient medium is one which comprises the micro- and macronutrients required to obtain a satisfactory growth of the microorganism in question and at the same time give rise to a sufficient production of the compound of the invention when subjected to suitable cultivation conditions.

Normally, a suitable nutrient medium contain sources of carbon and nitrogen assimilable by the microorganism and normally a low level of inorganic salts. In addition, the nutrient medium may contain traces of metals and other components necessary for the growth of the microorganisms and the production of the desired compound. Such other components may be in sufficient concentrations in the complex sources of carbon and nitrogen, typically used as nutrient sources, but can, of course, be added separately to the medium if desired.

The conditions under which the microorganism is cultivated may be chosen so as to optimize the production of secondary metabolites therefrom. The optimization of the production of secondary metabolites may be performed by methods known in the art, such as methods based on batch fermentation, fed-batch fermentation or continuous fermentation.

The composition of a suitable nutrient medium and suitable cultivation conditions for a given microorganism will be well known to the person skilled in the art.

The compound produced may be contained in the biomass or may alternatively be excreted into the culture medium, fully or partially, depending on the microorganism in question. In the case of a fungus, such as a fungus of the species Fusiccocum, especially the Fusiccocum sp. 1394-3 (IMI 351573), the compound is normally contained in the biomass, such as in or on the mycelium, the spores and the like.

The recovery of the compound of the invention from the biomass and/or culture medium produced in accordance with step a) above may be performed by any suitable technique useful for the microorganism in question. When the compound is contained in the biomass, e.g. a fungal mycelium, the recovery comprises harvesting the mycelium, e.g. by filtration and/or centrifugation, and subsequently isolating the compound therefrom. Suitable methods for isolating the compound includes extraction using a suitable solvent such as methanol, ethanol, ethyl acetate, or acetone, and solid phase extraction using a hydrophobic resin, an example of which is XAD-8 (Rohm and Haas Co.). Further purification may be accomplished by chromatography and crystallisation.

It may be desirable to produce derivatives of the compound recovered by this procedure, e.g. in order to improve certain properties of the metabolite, which are of crucial importance for its commercial success. As examples of properties, which may be desirable to improve, may be mentioned the solubility of the compound in aqueous media, the hydrophobicity, hydrophilicity, stability, specificity, toxicity, target spectrum, potency, heat resistance or UV resistance of the compound or the sensitivity of the compound to pH variations, etc. as well as membrane permeability and translocation of the compound in the host plant to which it is applied.

The derivatives may e.g. be produced by a chemical modification of the natural metabolite, by feeding suitable precursors to the medium in which the microorganism producing the metabolite is cultured, so as to obtain production of the desired derivative, by chemical synthesis using the native compound as a lead structure, or by genetic manipulation of the producer organism or its genetic material.

While it is contemplated that compounds of the invention having formula 3 or formula 4 may be prepared by the general method outlined above, i.e. from a microorganism capable of producing such compounds, it is presently preferred to prepare compounds of formula 3 and 4 from the compound of formula 5 produced as described above using a synthetic process.

Thus, ester derivatives of the compound of formula 5 being compounds of formula 3 (wherein $R^1$ is acyl) may be prepared by treating the compound of formula 5 dissolved in a suitable solvent with appropriate acylating reagents such as acid halides, acid anhydrides or activated esters, optionally under influence of a basic catalyst (pyridine, other amines etc.). Ether derivatives of the compound of formula 5 may be prepared by treating the compound of formula 5 dissolved in a suitable solvent with an appropriate alkylating reagent, such as a diazzo compound. Alternatively, appropriate alkyl halides and the like, under influence of a catalyst (potassium carbonate, silver oxide etc.) may be used as alkylating reagent, and the reaction performed in a suitable solvent like acetone, dimethylformamide etc.

Derivatives of the general formula 4 may be prepared from the compound with the formula 5 by addition of various nucleophilic species to C-5 in formula 3, such as appropriate oxygen-, sulphur-, nitrogen- and halogen nucleophiles, generated by well known methods.

It is also contemplated that compounds according to the invention whether of formula 3, 4 or 5 may be produced entirely by well known chemical synthetic processes using available starting materials.

The compounds of the invention have been found to exhibit antifungal activity, and they are consequently useful as active ingredients in fungicidal compositions.

The fungicidal composition of the invention normally contain novel compound of the invention as an active ingredient. However, in an alternative embodiment, the active ingredient of the fungicidal composition of the invention may be a fungus of a species belonging to the genus Fusicoccum capable of producing a compound of the invention, especially the Fusicoccum sp. (CMI CC No. 351573) or a mutant thereof capable of producing a compound of the invention. Also a fungal part, e.g. the mycelium, spores, and fruiting bodies containing or capable of producing a compound of the invention may be used as an active ingredient in a fungicidal composition of the invention.

The invention contemplates the use of any of these active ingredients used alone or in combination with any other of the compounds of the invention or any other biocidally active agent or plant growth regulator as active components in a fungicidal composition.

In order to provide the antifungal composition of the invention with a satisfactory antifungal activity, the active compound should normally be present in an amount of from 0.001 µg/ml to 100 mg/ml, such as from 0.05 µg/ml to 10 mg/ml, especially from 0.01 µg/ml to 5 mg/ml.

A fungicidal composition according to the invention having a fungicidally active compound of the invention as its active ingredient may for agronomical and/or horticultural applications be formulated by mixing the active principle with suitable inert and compatible carriers or diluents to obtain a composition of the type generally used in agricultural compositions such as a wettable powder, an emulsifiable concentrate, a concentrated emulsion, a granular formulation, a water soluble powder, a solution, a suspension concentrate, a release formulation (including a slow release formulation), an alginate, a xanthan gum and/or an aerosol. As solid carriers bentonite diatomaceous earth, apatite, gypsum, talc, pyrophyllite, vermiculite, ground shells, and clay may be mentioned. A surface active agent may also be added with the purpose of producing a homogeneous and stable formulation.

The diluent or carrier in the composition of the invention can as indicated be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Non-ionic agents include condensation products of fatty acid esters, fatty alcohols, fatty acid amides or fatty-alkyl- of alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a dispersible powder, an emulsifiable concentrate or granules. Moreover, it can be in a suitable form for direct application or as a concentrate or primary composition which requires dilution with a suitable quantity of water or other diluent before application.

An emulsifiable concentrate comprises the active ingredient dissolved in a water-immiscible solvent which is formed into an emulsion with water in the presence of an emulsifying agent.

A dusting powder comprises the active ingredient intimately mixed and ground with a solid pulverulent diluent, for example, kaolin.

A granular solid comprises the active ingredient associated with similar diluents to those which may be employed in dusting powders, but the mixture is granulated by known methods. Alternatively it comprises the active ingredient absorbed or adsorbed on a pre-granular diluent for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the active ingredient with water or other liquid, a wetting agent and suspending agent.

Depending on the circumstances such as the crop wherein fungi are to be controlled, the environmental conditions or other factors, a composition of the invention in addition to said fungicidally active compounds of the invention may also contain other active ingredients such as other biocides, such as fungicides, pesticides, herbicides, insecticides, nematocides, acaricides or plant nutrients or fertilizers.

Examples of other fungicides which can be combined with the active compounds of the invention include especially ergosterol biosynthesis inhibitors ("EBIs"). These are generally imidazole or triazole derivatives and examples include those known by the common names prochloraz, triadimefon, propiconazole, diclobutrazol, triadiminol, flusilazole, flutriafol, myclobutanil, penconazole, quinconazole, imazalil and diniconazole. Examples of non azole EBis include nuarimol, fenarimol, fenpropimorph, tridemorph and fenpropidine.

Other fungicides which can be combined with the enzyme preparation of the invention include:
Dithiocarbamates, e.g. thiram, maneb, zineb and mancozeb;
Phatalimides, e.g. captan, folpet and captafol;
Carboxines, e.g. carboxin and oxycarboxin;
Benzimidazoles, e.g. benomyl, carbendazim and fuberidazole;
Carbamates, e.g. prothiocarb and propamocarb;
Isoxazoles, e.g. hymexazol;
Cyanoacetamides, e.g. cymoxanil;
Ethylphosphonates, e.g. fosetylaluminium;
Phenylamides, e.g. furalaxyl, metalaxyl, benalaxyl, ofurace, cyprofuram and oxandixyl;
Dicarboximides, e.g. procymidone, iprodione and vinclozolin;
Organophosphorous fungicides, e.g. pyrazophos, triamiphos, ditalimfos and tolcofosmethyl; and
Aromatic hydrocarbon fungicides, e.g. quintozene, dichloren, and diphenyl.

In a further aspect the invention relates to a method of controlling fungi at a locus infested or liable to be infested therewith, which comprises applying to said locus a compound or a fungicidal composition of the invention as defined above.

Compounds of the invention has been found to be particularly potent towards fungi belonging to the class of Ascomycetes, Deuteromycetes or Oomycetes and accordingly, the locus to be treated with the fungicidal composition is one infected or liable to be infected with such fungi. Typically, the locus is selected from the group consisting of plants, timber, wood, cosmetics, feeds and foods.

Examples of fungal genera and species which have been found to or is expected to be sensitive to compounds of the invention (in vivo or in vitro) are fungi of the genera Phytophthora, especially *Phytophthora infestans* and *Phytophthora parasitica*, Plasmopara, especially *Plasmopara viticola* and *Plasmopara halstedii*, Saprolegnia, especially *Saprolegnia parasitica*, Pythium, Bremia, Pseudoperonospora, especially *Pseudoperonospora cubensis*, or Peronospora. Also fungi of the genii Botrytis, e.g. *Botrytis cinerea*, Aspergillus, e.g. *Aspergillus niger*, and Rhizoctonia, e.g. *Rhizoctonia solani*, have been found to be sensitive to compounds of the invention.

In connection with the method of the invention for controlling fungi, the fungicidal composition may for agronomical or horticultural uses be applied to a region to be treated either directly to the soil as a pre-emergence treatment or to the foliage or fruits of the plants as a pre- and/or post-emergence treatment. Depending on the crop and circumstances the treatment may be postponed until seeds or fruits appear on the plants, wherein fungi are to be controlled.

The active preparation or the compositions of the invention can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre-or post-emergence herbicide if this is thought necessary.

The concentration of the active compounds of the invention described herein in the compositions of the invention may vary within a wide range depending on the type of formulation and the field of application.

The concentration of the fungicidally active compounds of the invention in the compositions of the present invention when used alone or in combination with a conventional fungicide, as applied to plants is preferably within the range from about 0.001 to about 30 per cent by weight, especially 0.01 to 3.0 per cent by weight.

In a primary composition or concentrate the amount of active compound can also vary widely and can be, for example, in the range from about 5 to about 95 per cent by weight of the composition.

The concentration of the other fungicidally active ingredient in the mixed composition of the present invention, as applied to plants is preferably within the range of 0.001 to 50 per cent by weight, especially 0.01 to 10 per cent by weight. In a primary composition the amount of other active ingredient can vary widely and can be, for example, from 5 to 80 per cent by weight of the composition.

Sometimes, it is practicable to treat the roots of a plant before or during planting, for example by dipping the roots in a suitable liquid or solid composition. When the active preparation of the invention is applied directly to the plant a suitable rate of application is from 0.001 to 50 kg per hectare, preferably from 0.05 to 5 kg per hectare.

In the method of the invention the active preparation of the invention alone or in combination with a conventional biocide can also be applied to seeds or other habitats. Thus the preparation can be applied directly to the soil before, at or after drilling so that the presence of active ingredient in the soil can control the growth of fungi which may attack seeds.

The compositions may be applied in amounts corresponding to from about 1 g to about 50 kg fungicidally active compound per hectare.

When the soil is treated directly the active preparation alone or in a mixture with the conventional biocide can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.01 to 50 kg per hectare, more preferably from 0.05 to 5 kg per hectare.

Although the present invention has been described in detail in connection with controlling fungi in plants, it is also anticipated that the fungicidally active compounds of the invention may be used for controlling fungi in mammals, including humans; for the preservation of wood by adding said compounds to wood preservation and/or impregnation compositions; for the preservation of food or feed by adding the compounds directly to the food or feed or to the containers in which it is present; and for the preservation of cosmetics. Also, the active compounds of the invention may be useful as a fungicide and preservant in paints—both to prevent growth in the paint during storage, and growth on the painted object such as the plastered surface of a house—and as an additive to growth media, e.g. for cultivation of bacteria or yeast.

Furthermore, there are indications of antioxidant properties of the compounds of the invention. These may accordingly be used as antioxidant agents.

DEPOSITION OF MICROORGANISMS

For the purpose of describing this invention in detail a strain of the fungus Fusicoccum sp. (IMI CC No. 351573) has been deposited with the International Mycological Institute Culture Collection (IMI CC), Ferry Lane, Kew, Surrey TW9 3AF, England, for the purposes of patent procedure on the date indicated below. IMI CC being an international depository under the Budapest Treaty affords permanence of the deposit in accordance with rule 9 of said treaty.

Deposit date: 4 Feb. 1992

Depositor's ref.: L394-3

IMI CC designation IMI CC No. 351573

IMI CC No. 351573 belongs to the class Deuteromycetes, subclass Coelomycetidae, order Sphaeropsidales. The fungus was isolated from the plant *Asphodelus microcarpus* collected in the Mediterranean area.

The present invention is further illustrated in the following examples which are not intended, in any way, to limit the scope of the invention as claimed. Various modifications of the invention in addition to those shown and described herein will from the foregoing description be apparent to those skilled in the art. Such modifications are intended to fall within the scope of the appended claims.

EXAMPLES

Example 1

Fermentation

A slant culture of the fungus Fusicoccum sp. (IMI CC No. 351573) grown on potato dextrose agar (12 ml/slant) for 6 days at room temperature was mixed with 10 ml of sterile water. 3 ml thereof was inoculated into 500 ml Erlenmeyer flasks containing 100 ml of Yeast-Extract-Sucrose medium, prepared by mixing 1000 ml of distilled water, 20 g of yeast-extract (Difco), 150 g of sucrose, 1 ml of trace metal solution (8.9 g of $ZnSo_4 \cdot 7H_2O$ and 3.9 g of $CuSO_4 \cdot 5H_2O$ dissolved in 500 ml of distilled water), adjusting the pH to 6.4 and autoclaving the resulting substrate at 121° C. for 40 minutes. After inoculation the flasks were shaken at 200 rpm for 6 days at 26° C.

Example 2

Isolation and Characterization of the Compound Having the Formula 5

The mycelium from two liters of culture broth (20 flasks) obtained as described in Example 1 was separated by centrifugation and extracted thrice with 0.75 liter portions of EtOAc for two hours under vigorous mechanical stirring. The combined extracts containing the compound of interest were filtered through filter paper to remove residual solids and subsequently dried by freezing at −18° C. and removal of the separated ice by filtration. Evaporation to dryness under reduced pressure yielded a brownish, semi-crystalline residue (5.0 g). This residue was taken up in a small volume of chloroform and applied to a column of silica gel (Merck $SiO_2$ 60, 63–200 μm, 300×40 mm), packed in EtOAc. Elution with EtOAc and collection of the fast moving yellow band afforded after evaporation 1.05 g of the crude metabolite. Crystallization from EtOAc, by slow evaporation of the solvent at 4° C., yielded a homogeneous material (470 mg) in the form of long yellow needles, m.p. 113°–114° C. (Found: C 57.21; H 4.78. Calc. for $C_8H_8O_4$: C 57.14; H 4.80); UV nm(ε) in MeOH: 283(13400), 330(sh); IR $v_{max}cm^{-1}$ in KBr: 1776, 1686, 1646, 1580, 1451, 1435, 1376, 1354, 1285, 1244, 1157, 1022, 966, 862, 754, 616. EI-MS m/z (rel.int. %): 168 (20), 153 (2), 126 (3), 85 (100), 83 (19), 69 (11) 55 (7), 43 (34).

For the sake of convenience, the compound of formula 5 is termed compound 5 hereinafter. NMR-data are presented in table 1.

TABLE 1

| $^{13}$ c— and $^1$H—NMR data ($CDCl_3$) for Compound 5 | | | |
|---|---|---|---|
| No. | $\delta_C{}^a$ | $\delta_H{}^b$ | $J_{CH}{}^c$ |
| 1 | 168.6 | — | $J_{1,8}$ = 5.0 |
| 2 | 104.0 | — | $J_{2,8}$ = 7.0; $J_{2,OH}$ = 6.0$^d$ |
| 3 | 161.3 | — | $J_{3,8\,=\,4.4}$; $J_{3,OH}$ = 4.8$^d$; $J_{3,5}$ = 6.4 |
| 4 | 159.6 | — | $J_{4,OH}$ = <1.0$^d$; $J_{4,5}$ = 6.2 |
| 5 | 107.1 | 6.33(s) | $J_{5,5}$ = 161.2; $J_{5,7}$ = 1.7 |
| 6 | 203.5 | — | $J_{6,5}$ = 2.9; $J_{6,7}$ = 5.9 |
| 7 | 31.5 | 2.48(s) | $J_{7,7}$ = 128.6 |
| 8 | 6.4 | 1.86(s) | $J_{8,8}$ = 130.1 |

$^a$in ppm relative to TMS (0.0 ppm) at 75.47 Mhz, 297K.
$^b$in ppm relative to TMS (0.0 ppm) at 300.13 MHz, 297K
$^c J_{n,m}$ defines the coupling in Hz between C-n and H-m (or OH at δ 13.04)
$^d$Non-observable after exchange with $D_2O$

Example 3

Preparation of a Methanol Adduct of Compound 5 (=A Compound of Formula 4 Wherein $R^1$=H and Nu=OMe)

Compound 5 (75 mg) obtained as described in Example 1 was dissolved in MeOH (5 ml) and stirred at room temperature for 48 hrs. The solvent was removed under reduced pressure and purified by silica gel chromatography using ethylacetatemethanol (10:1) as eluent. After evaporation of the solvent the product (60 mg) was obtained as an yellowish oil. $^1$H- (300.13 MHz) and $^{13}$C-NMR (75.47 MHz) data in CDCl$_3$ were as follows (δ-values in ppm relative to the solvent signal at 7.27 and 77.0 ppm, respectively): $^1$H: 1.78(3H,s), 2.38(3H,s), 2.90(1H,d,18Hz), 3.21(3H,s), 3.70(1H,d,18Hz) and 10.3(1H,s,broad). $^{13}$C: 5.6, 31.3, 50.3, 50.8, 100.9, 101.4, 168.0, 171.3 and 210.6.

Example 4

Preparation of a Benzylether Derivative of Compound 5 (=A Compound of Formula 3 Wherein $R^1$=CH$_2$C$_6$H$_5$)

After dissolving compound 5 (50 mg) in dimethylformamide (5 ml), K$_2$CO$_3$ (46 mg) and benzylbromide (42 µl, 60 mg) were added and, after flushing with nitrogen, the mixture was stirred for 20 hrs. at room temperature. After addition of water (25 ml) the crude product was extracted with dichloromethane (2×25 ml) and washed with water. The combined organic extracts were dried (Na$_2$SO$_4$) and the solvent evaporated. The product was purified by preparative TLC (silica gel, hexan-ethylacetate 4:1) and crystallized from ether as brownish crystals (mp. 116°–17° C.). $^1$H-(300.13 MHz) and $^{13}$C-NMR (75.47 MHz) data in CDCl$_3$ were as follows (δ-values in ppm relative to the solvent signal at 7.27 and 77.0 ppm, respectively): $^1$H: 2.07 (3H,s), 2.25(3H,s), 5.40(2H,s), 6.07(1H,s) and 7.38(5H,m). $^{13}$C: 9.2, 31.9, 74.0, 105.4, 110.2, 127.4, 128.8, 128.9, 134.6, 148.0, 160.3, 169.3 and 197.6.

Example 5

In vitro Fungicidal Activity

The fungicidal activity of compound 5 of the invention was determined in an in vitro assay performed substantially as described in Danish patent application No. DK 583/92 using various Deuteromycetes and Ascomycetes as test organisms.

The assay was carried out as follows:

In agar plates containing the test organisms embedded in agar, small wells were punched, and 15 µl of solutions containing various concentrations of compound 5 prepared as described in Example 1 above were applied to each well. The plates were incubated for two days at room temperature before clearing zones indicating inhibition of the test organism were measured. The results are shown in Table 2, in which a "4" denotes a clearing zone of more than 25 mm, a "3" a zone between 15 and 25 mm, a "2" a zone between 10 and 15 mm, a "1" a zone between 0 and 10 mm and a "0" denotes that no clearing zone was observed.

TABLE II

|  | 1.0 mg/ml | 0.1 mg/ml | 0.01 mg/ml |
| --- | --- | --- | --- |
| Botrytis cinerea | 4 | 3 | 1 |
| Rhizoctonia solani | 3 | 2 | 0 |
| Aspergillus niger | 2 | 1 | 0 |

MIC$_{50}$ was determined to be about 0.2 µg/ml for *Phytophthora infestans*.

The inhibitory activity against Pythium and *Phytophthora infestans* was estimated using a microtiter assay:

1 ml of a liquid medium was applied to each well in a 24 well microtiter plate. For the Pythium assay the medium had the following composition: 0.9 ml diluted salt solution (Dill, B. C. & M. S. Fuller (1971) Archiv. Microb. 87: 92–98) and 0.1 ml of Yeast Peptone glucose broth which were mixed before application. For the Phytophthora assay, the medium had the following composition: 0.9 ml diluted salt solution and 0.1 ml Pea suspension which were mixed before application.

Subsequently, a 20 µl sample of each concentration of antifungal compound was applied to each well followed by 100 µl of a sporangia suspension for the *P. infestans*, and 100 µl of a zoospore suspension for the Pythium assay.

Microtiter plates with *P. infestans* were incubated in diffuse light at 17°–20° C. After 3 days fungal growth was estimated.

Microtiter plates with Pythium were incubated at 30° C. After 1 day the fungal growth was estimated. The results are shown in Table 3, in which "4" denotes total inhibition an "0" no inhibition of the growth of the test organism.

TABLE III

|  | 1.0 mg/ml | 0.1 mg/ml | 0.01 mg/ml |
| --- | --- | --- | --- |
| Phytophthora | 4 | 4 | 4 |
| Pythium sp. | 4 | 4 | 1 |

LIST OF REFERENCES CITED IN THE SPECIFICATION (1) Pattenden, G., Fortschritte der Chemie Organischer Naturstoffe, 35 pp. 133–198 (1978)

(2) Turner, R. W. in DE 2101 637

(3) Rehse, K. and Ermisch, U., Archiv der Pharmazie, 316 pp. 115–20 (1983)

(4) Ballio et al. "Occurrence of fusicoccin in plant tissues infected by *Fusicoccum amygdali* Del." Physiol. Plant. Path: 8, 163 (1976)

(5) Ballio et al., "Characterization of By-Products of Fusicoccin in Culture Filtrates of *Fusicoccum amygdali* Del.", Experientia: 26, 349–51, (1970)

(6) Ballio et al., "A new cerebroside from *Fusicoccum amygdali* Del." Biochemica et Biophysica Acta: 573, 51 (1979)

We claim:

1. A compound having the formula 3

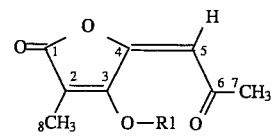

Formula 3 wherein $R^1$ is hydrogen, straight or branched alkyl with 1–10 carbon atoms, straight or branched alkenyl with 2–10 carbon atoms, straight or branched alkynyl with 2–10 carbon atoms, benzyl or aryl, optionally mono- or plurisubstituted with straight or branched alkyl with 1–10 carbon atoms, hydroxy, alkoxy, halogen, an amino or a nitro group; and when $R^1$ is H salts thereof, or $R^1$ is acyl ($R^1$=—COR$^2$) wherein $R^2$ is straight or branched alkyl with 1–10 carbon atoms, alkenyl with 2–10 carbon atoms, alkynyl with 2–10 carbon atoms, or aryl, optionally mono- or plurisubstituted with alkyl with 1–10 carbon atoms, hydroxy, alkoxy, halogen, an amino or a nitro group.

2. The compound according to claim 1, wherein $R^1$ is hydrogen, methyl, benzyl or acetyl.

3. A compound having the formula 5

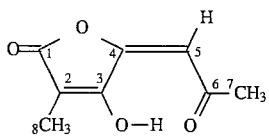

Formula 5 and salts thereof.

4. A compound having the formula 4

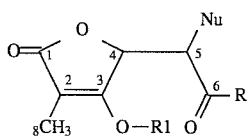

Formula 4 wherein $R^1$ is as defined in claim 1 and Nu is halogen or —$OR^3$, —$SR^3$, —$NR^3R^{3'}$, wherein $R^3$ and $R^{3'}$, being identical or different, has the same meaning as $R^1$ as defined in claim 1, and salts thereof.

5. A compound according to claim 4, wherein $R^1$ is hydrogen and Nu is —$OCH_3$.

6. A method of preparing a compound according to claim 1 comprising (a) cultivating a species belonging to the genus Fusicoccum on a nutrient media, and (b) recovering the compound from said medium.

7. A method according to claim 6, which further comprises c) chemically modifying the compound obtained in step b).

8. A method according to claim 6, wherein the fungus is the Fusicoccum sp. (IM CC No. 351573) or a mutant thereof capable of producing the compound.

9. A method of controling fungi at a locus infested or liable to be infested therewith, which comprises applying to said locus a compound according to claim 1.

10. The method of claim 9, in which the locus is selected from the group consisting of plants, timber, cosmetics, feed, paint, growth media, and foods.

11. The method according to claim 9, in which the fungus to be controlled is a plant pathogenic fungus.

12. The method according to claim 11, in which the fungus to be controlled belongs to the genera Phytophthora Plasmopara, Pythium, Bremia, Pseudoperonospora, Saprolegnia, Botrytic, Aspergillus, Rhizoctonia or Peronospora.

13. A method according to claim 6, wherein the Fusicoccum sp. is one found on a plant belonging to the genus Asphodelus.

14. A method according to claim 6 wherein the Fusicoccum sp. is on found on a plant of the species *A. microcarpus.*

15. The method according to claim 9 in which the fungus to be controlled is a plant pathogenic fungus which belongs to a class selected from the group consisting of Ascomycetes, Deuteromycetes or Oomycetes.

16. The method according to claim 9 in which the fungus to be controlled is selected from the group consisting of *Phytophthora infestans* and *Plasmopara viticola.*

17. A fungicidal composition comprising, as an active ingredient, a compound according to claim 1.

18. The composition of claim 17, wherein said compound is present in an amount of from 0.001 μg/ml to 100 mg/ml.

19. A fungicidal composition comprising as an active ingredient a compound of claim 1 in combination with another active agent selected from the group consisting of a fungicidal agent, pesticidal agent and growth regulator, in which the active agent is present in an amount of 0.001 to 50% by weight.

20. The fungicidal composition according to claim 19 wherein other active agent(s) is/are present in an amount of 0.001 to 50% by weight, the other active agent is present in an amount of 0.01 to 10% by weight.

21. The composition according to claim 17 in which the compound is obtained from a fungus of a species belonging to the genus Fusicoccum.

22. The composition according to claim 17 in which the compound is obtained from a fungus is Fusicoccum sp. (CMI CC No. 351573) or a mutant capable of producing said compound.

23. An isolated pure culture of the microorganism Fusicoccum sp. (CMI CC No. 351573) or a mutant thereof capable of producing a compound as defined in claim 1.

* * * * *